March 30, 1976 A. GROB Plant Pat. 3,851
KALANCHOE PLANT
Filed Sept. 25, 1974
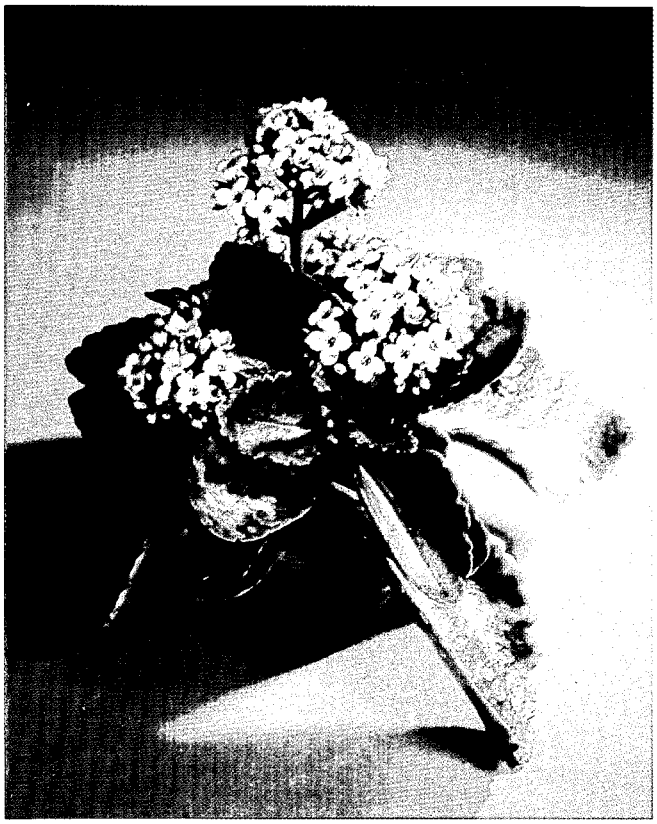

United States Patent

Plant Pat. 3,851

Patented Mar. 30, 1976

3,851

KALANCHOE PLANT

Adolf Grob, St. Gallen, Switzerland, assignor to Mikkelsens Inc., Ashtabula, Ohio Filed Sept. 25, 1974, Ser. No. 509,132

Int. Cl. A01h *5/00*

U.S. Cl. Plt.—68 1 Claim

The present invention relates to a new and distinct variety of Kalanchoe plant known by the varietal name Rotkappchen.

The new variety was discovered by me as a selected, cultivated seedling derived from self-crossing of the unpatented cultivar of Kalanchoe known by the varietal name Grobs Exotica. The new cultivar was discovered by virtue of its noticeably shorter growth and intensive large flower umbels. The new cultivar was first asexually reproduced by vegetative cuttings at St. Gallen, Switzerland, and the unique characteristics of the new cultivar have been transmitted through successive propagations.

The new cultivar is particularly characterized by its bright orange-scarlet colored flowers, large single umbels and relatively short response time. The new cultivar is particularly suitable for flowering from April to November under controlled greenhouse culture, and response time for the new cultivar upon initiation of short days is 10–11 weeks in summer and 12–13 weeks in winter. With controlled greenhouse culture, the new cultivar can be brought to flowering during the entire year.

With respect to the cultivar Feuerzauber, disclosed in my pending application Ser. No. 509,143, filed Sept. 25, 1974 and perhaps the closest cultivar for comparison purposes, the new cultivar has a more vigorous growth habit, large single umbels and larger single petals and has an orange-scarlet flower color. In addition, it flowers approximately 10 days earlier.

The following description is based on plants of the new cultivar grown initially in St. Gallen, Switzerland, and subsequently in Ashtabula, Ohio. Flower color and foliage values are taken from RHS Colour Chart.

The accompanying color photographic drawing shows a typical blooming plant of the new cultivar, with the color being as true as possible with color illustrations of this type.

Parentage: The new cultivar is a seedling resulting from self-crossing the parent Grobs Exotica, an unpatented cultivar.

Propagation: By asexually propagating by cuttings, it has been successfully demonstrated that the new cultivar is stable and produces true to type.

Form: Bush form; medium tall; numerous branches; upright.

Growth habit: Medium vigor; upright and branching.

Rooting: The roots of the new cultivar are good and strong.

Blooming habit: Early response, reacts well to short day treatment.

Blooming season: Natural blooming season is January–February, although by short day treatment, flowering of the cultivar is possible year around. The new cultivar needs a greater amount of light to prevent flowering in winter months compared to other Kalanchoes. The response time is relatively short, 10–11 weeks in summer and 12–13 weeks in winter.

Foliage: Leaves are opposite, borne at nearly right angles to the stem to 20°–30° above the horizontal; internodal distance is average for Kalanchoes, uniform green color, glabrous.

*Size.*—Similar to the Grob cultivars Feuerzauber and Feuerball, measuring approximately 5–6 cm. wide by 7–8 cm. long. The cultivar Feuerball is disclosed in my pending application Ser. No. 509,145, filed Sept. 15, 1974.

*Shape.*—Elliptical to oval.

*Texture.*—Smooth, thick, fleshy, crisp, coriaceous.

*Margin.*—Toward crenate, usually cupping upward with some twisting.

*Color.*—Upperside, from 146A to 147A. Underside, nearly 146B.

Disease resistance: No evidence of susceptibility to known diseases to date. When grown with Exotic Gold or Exotic Yellow infected with mildew, Rotkappchen shows no signs of becoming infected.

Flowers:

*Borne.*—On compound terminal paniculate cymes. Main flower stems measure approximately 10 cm. to 12 cm. and are vigorous and strong in all seasons; individual flower pedicels are short and stalky, inflorescence is compact, 6 to 10 nodal flowering shoots developing below the main apical inflorescence.

*Quantity.*—Overall quantity of flowers in each cyme is very high as individual flowers keep developing over a period of three to four months.

*Flower buds.*—Are full, firm and well formed, covered with four sepals, measuring approximately 12 to 14 mm. just as the petals begin to emerge.

*Petals.*—Four petals with little or no overlapping, measuring 6 mm. wide by 10 mm. long and being uniform in shape; total flower diameter 18 to 20 mm., color orange-red 33A, reverse mixed with red near orange-red 33C.

Reproductive organs:

*Stamens.*—Normally eight in number, occasionally nine or ten; filaments green, anthers brown.

*Pollen.*—Light yellow—abundant.

*Styles/ovaries.*—Light green, stigmas turn crystalline white when receptive—four carpels producing multiple seeds of good quality.

I claim:

1. A new and distinct type of Kalanchoe plant characterized particularly by its orange-scarlet flower color, vigorous growth habit, large single petals and umbels, and by its relatively early flowering habit.

No references cited.

ROBERT E. BAGWILL, Primary Examiner